United States Patent
Grill et al.

(10) Patent No.: US 11,298,546 B2
(45) Date of Patent: Apr. 12, 2022

(54) SYSTEMS AND METHODS FOR MINIMIZING RESPONSE VARIABILITY OF SPINAL CORD STIMULATION

(71) Applicant: Duke University, Durham, NC (US)

(72) Inventors: Warren Grill, Durham, NC (US); John Gilbert, Durham, NC (US)

(73) Assignee: Duke University, Durham, NC (US)

( * ) Notice: Subject to any disclaimer, the term of this patent is extended or adjusted under 35 U.S.C. 154(b) by 49 days.

(21) Appl. No.: 16/217,787

(22) Filed: Dec. 12, 2018

(65) Prior Publication Data

US 2019/0175916 A1 Jun. 13, 2019

Related U.S. Application Data

(60) Provisional application No. 62/597,606, filed on Dec. 12, 2017.

(51) Int. Cl.
*A61N 1/36* (2006.01)
*A61N 1/05* (2006.01)
(Continued)

(52) U.S. Cl.
CPC ....... *A61N 1/36185* (2013.01); *A61N 1/0551* (2013.01); *A61N 1/36071* (2013.01);
(Continued)

(58) Field of Classification Search
CPC ...... A61N 1/36; A61N 1/3605; A61N 1/3606; A61N 1/36062; A61N 1/36071; A61N 1/36075; A61N 1/36135; A61N 1/36171; A61N 1/05; A61N 1/0551; A61N 1/0553; A61N 1/36146; G16H 20/30
(Continued)

(56) References Cited

U.S. PATENT DOCUMENTS 7,305,268 B2 * 12/2007 Gliner .................. A61N 1/0531
607/45
7,463,927 B1 12/2008 Chaouat
(Continued)

FOREIGN PATENT DOCUMENTS

WO WO/2014/159880 A1 10/2014
WO WO 2016/069157 A1 5/2016
(Continued)

OTHER PUBLICATIONS

Zhang et al., "Modeling effects of spinal cord stimulation on wide-dynamic range dorsal horn neurons: influence of stimulation frequency and GABAergic inhibition," 2014, *J Neurophysiol* 112: 552-567.
(Continued)

*Primary Examiner* — Ahmed M Farah
(74) *Attorney, Agent, or Firm* — Casimir Jones, S.C.; Peter J. Schlueter

(57) ABSTRACT

This present disclosure provides systems and methods relating to neuromodulation. In particular, the present disclosure provides systems and methods for identifying optimized temporal patterns of spinal cord simulation (SCS) for minimizing variability in patient responses to SCS. The systems and methods of neuromodulation disclosed herein facilitate the treatment of neuropathic pain associated with various disease states and clinical indications.

29 Claims, 10 Drawing Sheets

(51) Int. Cl.
  *G16H 20/30* (2018.01)
  *A61N 1/372* (2006.01)
(52) U.S. Cl.
  CPC ..... *A61N 1/36135* (2013.01); *A61N 1/36146* (2013.01); *G16H 20/30* (2018.01); *A61N 1/37241* (2013.01)
(58) Field of Classification Search
  USPC .......................... 607/46, 115–118; 128/898
  See application file for complete search history.

(56) References Cited

U.S. PATENT DOCUMENTS

| | | | | |
|---|---|---|---|---|
| 8,224,453 | B2 * | 7/2012 | De Ridder | A61N 1/36153 607/46 |
| 8,447,405 | B2 * | 5/2013 | Grill | A61N 1/36067 607/45 |
| 10,213,605 | B2 * | 2/2019 | Grill | A61N 1/36139 |
| 10,232,179 | B2 * | 3/2019 | Grill | A61N 1/36071 |
| 10,702,696 | B2 * | 7/2020 | Grill | A61N 1/36062 |
| 10,842,989 | B2 * | 11/2020 | Brill | G16H 40/63 |
| 2015/0238765 | A1 | 8/2015 | Zhu | |
| 2016/0022993 | A1 | 1/2016 | Grill et al. | |
| 2017/0056642 | A1 | 3/2017 | Moffitt et al. | |

FOREIGN PATENT DOCUMENTS

| | | |
|---|---|---|
| WO | WO 2016/182894 A1 | 11/2016 |
| WO | WO 2017/0210491 | 12/2017 |

OTHER PUBLICATIONS

International Search Report and Written Opinion of PCT/US2018/065176 dated Mar. 18, 2019, 16 pages.

* cited by examiner

SYSTEMS AND METHODS FOR MINIMIZING RESPONSE VARIABILITY OF SPINAL CORD STIMULATION

RELATED APPLICATIONS

This application claims priority to and the benefit of U.S. Provisional Patent Application No. 62/597,606 filed Dec. 12, 2017, which is incorporated herein by reference in its entirety for all purposes.

FIELD

This present disclosure provides systems and methods relating to neuromodulation. In particular, the present disclosure provides systems and methods for identifying optimized temporal patterns of spinal cord simulation (SCS) for minimizing variability in patient responses to SCS. The systems and methods of neuromodulation disclosed herein facilitate the treatment of neuropathic pain associated with various disease states and clinical indications.

BACKGROUND

Spinal cord stimulation (SCS) involves the therapeutic application of electrical pulses using a surgically implanted device to treat chronic pain. The device is typically implanted near a targeted area of the spinal cord. Unfortunately, patient responses to SCS-based therapy are highly variable and depend on a number of factors, including the anatomy of the spine and spinal cord, electrode position, and the origin, location and characteristics of pain.

These factors, among others, contribute to the variance in patient responses to SCS (e.g., degree of pain relief). Changing the amplitude, pulse duration, and timing of the applied electrical pulses modulates the effectiveness of SCS in relieving pain, but the breadth of this parameter space makes optimizing programming for specific patients a significant clinical challenge. Furthermore, evaluating SCS performance is difficult because patients have a broad range of parameter settings and different device programmers use different protocols to select parameters. Additionally, the location and characteristics of pain as well as the effectiveness of any particular set of stimulation parameters vary over time, and these factors also contribute to the variance of patient responses to SCS.

SUMMARY

Embodiments of the present disclosure include a method of identifying an optimized spinal cord simulation (SCS) pattern for pain reduction. In accordance with these embodiments, the method includes generating a plurality of SCS patterns using an optimization algorithm based on predetermined performance criteria, evaluating the plurality of SCS patterns for pain reduction using a computational model of a neuronal network, and identifying at least one candidate SCS pattern having an optimized temporal pattern of stimulation capable of reducing pain.

In some embodiments, the plurality of SCS patterns are generated for at least one of efficiency optimization, efficacy optimization, and variance optimization. In some embodiments, the optimized SCS pattern reduces pain in a plurality of subjects with different pain states. In some embodiments, the optimized SCS pattern comprises a temporal pattern of electrical stimulation pulses.

In some embodiments, the temporal pattern of electrical stimulation pulses comprises a non-regular temporal pattern with one or more varying inter-pulse intervals. In some embodiments, the optimized SCS pattern comprises a stimulation frequency ranging from about 1 Hz to about 200 Hz. In some embodiments, the optimization algorithm comprises at least one of a genetic algorithm, a particle swarm algorithm, a simulated annealing algorithm, an ant colony algorithm, an estimation of distribution algorithm, a gradient descent algorithm, and any combinations and derivations thereof.

In some embodiments, the predetermined performance criteria are incorporated into a fitness function used to evaluate the fitness of the plurality of SCS patterns. In some embodiments, the predetermined performance criteria comprise at least one of: i) reduction in pain score; ii) SCS pattern efficiency; and iii) variance of pain score reduction across different pain states.

In some embodiments, the reduction in the pain score comprises a change in firing rate and/or firing pattern of one or more neurons in the computational model. In some embodiments, the SCS pattern efficiency is proportional to the average frequency of stimulation. In some embodiments, the variance of pain score reduction across different pain states corresponds to variance of the response to SCS across a population of computational models of a neuronal network. In some embodiments, the response to SCS comprises a change in firing rate and/or firing pattern of one or more neurons in the computational model. In some embodiments, the computational model of the neuronal network is coupled to the optimization algorithm by the predetermined performance criteria. In some embodiments, the computational model of the neuronal network simulates activity of a wide dynamic range (WDR) neuron. In some embodiments, the activity of the WDR neuron in the computational model is a proxy for pain. In some embodiments, the computational model of the neural network comprises three network zones comprising heterogeneous inhibitory and excitatory neural connections. In some embodiments, the computational model of the neural network simulates a network state by varying at least one of: a biophysical input parameter, a stimulation input parameter, and a mechanism input parameter.

In some embodiments, the computational model simulates a pain state of a subject by varying the at least one biophysical input parameter, and wherein the at least one biophysical input parameter comprises: i) reversal potential of inhibitory synapses within each network zone; ii) maximum conductance of GABAergic synapses within each network zone; iii) maximum conductance of AMPA synapses onto inhibitory neurons within each network zone; and iv) number of C fibers activated in each surround zone.

In some embodiments, the reversal potential of inhibitory synapses ranges from about −50 mV to about −100 mV. In some embodiments, the maximum conductance of GABAergic synapses ranges from about 50% to about 100%. In some embodiments, the maximum conductance of AMPA synapses onto inhibitory neurons ranges from about 50% to about 100%. In some embodiments, the number of C fibers activated in each surround zone ranges from about 0% to about 50%. In some embodiments, the computational model simulates a response to an SCS pattern by varying the at least one stimulation input parameter, and wherein the at least one stimulation input parameter comprises: i) number of fibers activated within each network zone by an SCS pattern; and ii) stimulation frequency of an SCS pattern within each network zone. In some embodiments, the number of fibers activated within each network zone by the SCS pattern ranges from about 0% to about 100% in a first network zone, from about 0% to about 100% in a second network zone, and from about 0% to about 100% in a third network zone. In some embodiments, the stimulation frequency within each network zone ranges from about 1 Hz to about 200 Hz.

In some embodiments, the computational model simulates a response to an SCS pattern by varying the at least one mechanism input parameter, and wherein the at least one mechanism input parameter comprises: i) maximum sodium conductance; and ii) maximum potassium conductance. In some embodiments, the maximum sodium conductance ranges from about 50% to about 150% within a network zone. In some embodiments, the maximum potassium conductance ranges from about 50% to about 150% within a network zone.

Embodiments of the present disclosure also include a system for delivering spinal cord stimulation (SCS) to reduce pain. In accordance with these embodiments, the system includes an electrode sized and configured for implantation in proximity to neural tissue, and a pulse generator coupled to the electrode. In some embodiments, the pulse generator includes a power source comprising a battery and a microprocessor coupled to the battery. In some embodiments, the pulse generator is configured to generate electrical signals for delivering an SCS pattern having an optimized temporal pattern of electrical stimulation capable of reducing pain.

In some embodiments, the optimized SCS pattern reduces pain in a plurality of subjects with different pain states. In some embodiments, the optimized SCS pattern comprises non-regular temporal patterns with one or more varying inter-pulse intervals. In some embodiments, delivering an SCS pattern having an optimized temporal pattern of electrical stimulation comprises delivering one or more SCS patterns to one or more electrodes.

Embodiments of the present disclosure also include a method for delivering spinal cord stimulation (SCS) to reduce pain using the systems described above. In accordance with these embodiments, the method includes programming the pulse generator to output the optimized SCS pattern, and delivering the SCS pattern to a subject to reduce pain.

In some embodiments, the optimized SCS pattern reduces pain in a plurality of subjects with different pain states. In some embodiments, the optimized SCS pattern comprises non-regular temporal patterns with one or more varying inter-pulse intervals. In some embodiments, delivering an optimized SCS pattern to a subject comprises delivering one or more different SCS patterns to one or more different neuronal populations.

BRIEF DESCRIPTION OF THE DRAWINGS

FIG. 2A: Synaptic connections for each neuron in the model are shown. FIG. 2B: Network architecture within the model for a single node. Primary afferents (Aβ, Aδ, and C) transmit inputs to local inhibitory (IN) and excitatory (EX) interneurons and a wide dynamic range (WDR) projections neuron. SCS is represented as a constant frequency input to the dorsal columns that moves antidromically along the Aβ fibers. The output of the node is the firing rate of the WDR neuron. FIG. 2C: Distributed multi-nodal model architecture. Each circle represents a node of the model from FIG. 2B with unique inputs. The center node (Zone 1) receives excitatory inputs from zone 2 nodes and inhibitory inputs from both Zone 2 and Zone 3 nodes. All connections between nodes are from interneurons to WDR neurons. Connections represented in the model are bidirectional (e.g., Zone 2 excitatory interneurons project to the Zone 1 WDR neuron and the Zone 1 excitatory interneuron projects back to Zone 2 WDR neurons). The model is extended to eliminate edge effects for the center node. FIG. 2D: Representation of receptive field with multiple zones on a rat foot.

FIG. 4 includes representative Monte Carlo simulations used to determine the effect of individual parameters on the response of model neurons to SCS.

Temporal patterns of stimulation are the inputs to the model. The algorithm evaluates the fitness of the pattern based on how much they reduce pain in the model, the efficiency of the pattern, and the reduction in variance of the pain score across multiple trials. The pain score in the model is proportional to the firing rates of the WDR neurons. The algorithm designs new patterns of stimulation based on the patters with the highest fitness from the previous round.

Figure 7A:
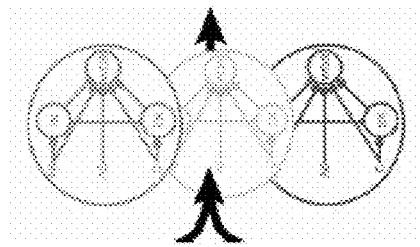
Figure 7B:
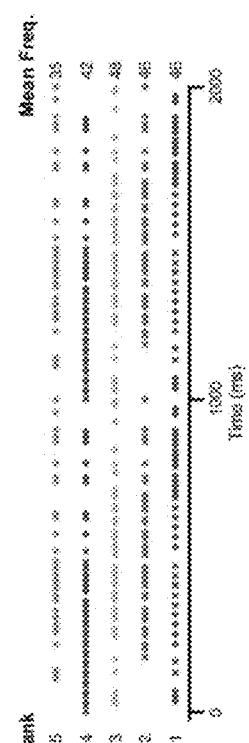
Figure 7C:
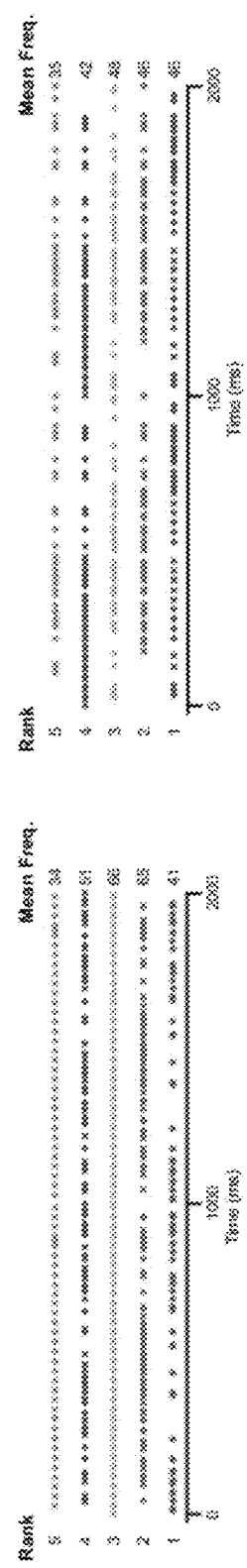

FIGS. 7A-7C include a representative genetic algorithm run across multiple network states (FIG. 7A), and a representative graph showing the range of performance scores across network states for the best temporal pattern of SCS as the algorithm evolves (FIG. 7B). Decreasing scores as indicated by the placement of the bar along the y-axis in the plot represent increases in the efficacy of the patterns while reductions in the range of scores decreases the variance in efficacy across states. FIG. 7C: Examples of the top five performing 1000 ms long temporal patterns of SCS evolving between the $1^{st}$ and $25^{th}$ generation of the genetic algorithm.

Figure 6:
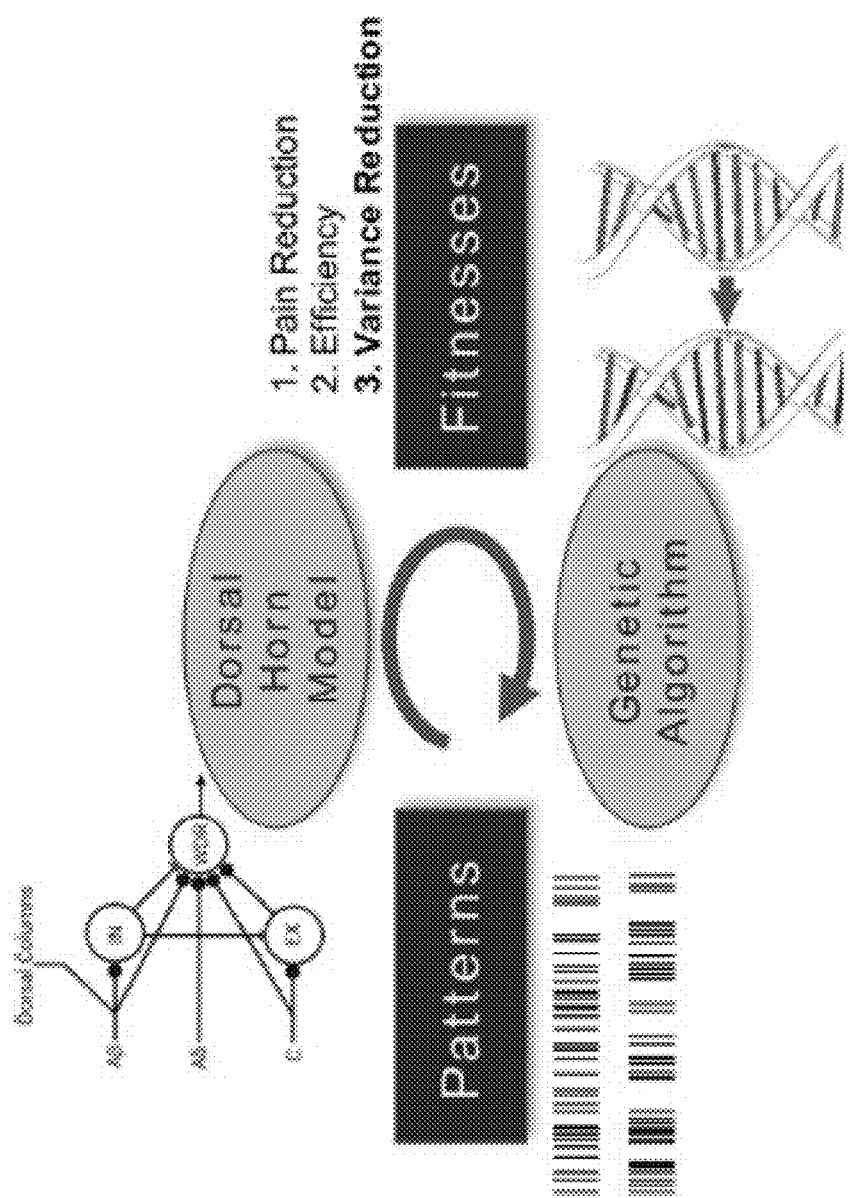
FIG. 6 includes a representative method for producing a temporally optimized SCS pattern using a genetic algorithm.
Figure 8A:
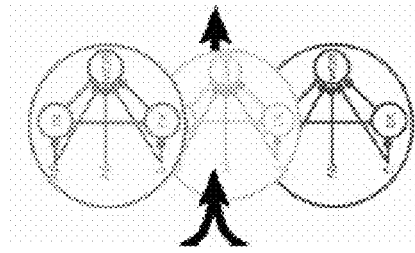
Figure 8B:
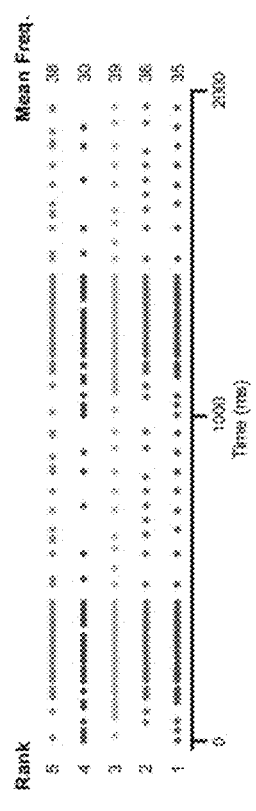
Figure 8C:
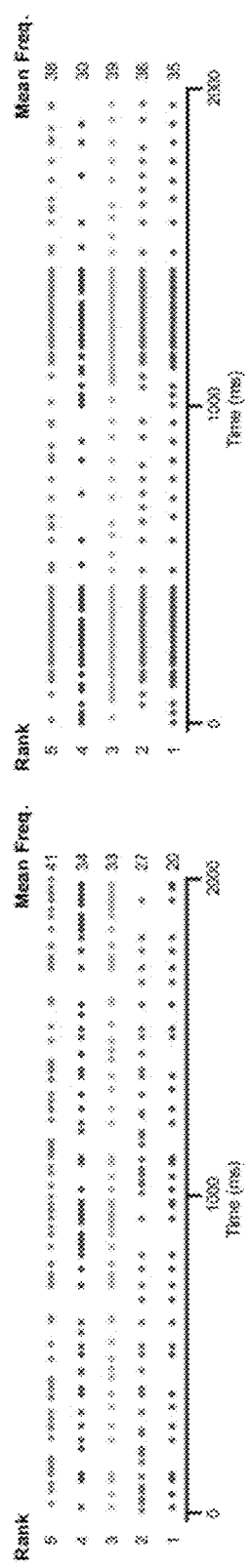

FIGS. 8A-8C include a representative genetic algorithm run across multiple network states (FIG. 8A) with a different scoring function from the run shown in FIGS. 7A-7C. The changes are due to changing the relative weights of the components in the scoring function (FIG. 6). FIG. 8B: A representative graph showing the range of performance scores across network states for the best temporal pattern of SCS as the algorithm evolves. Decreasing scores as indicated by the placement of the bar along the y-axis in the plot represent increases in the efficacy of the patterns while reductions in the range of scores decreases the variance in efficacy across states. FIG. 8C: Examples of the top five performing 1000 ms long temporal patterns of SCS evolving between the $1^{st}$ and $50^{th}$ generation of the genetic algorithm.

DETAILED DESCRIPTION

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated. Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

"Pain" generally refers to the basic bodily sensation induced by a noxious stimulus, received by naked nerve endings, characterized by physical discomfort (e.g., prickling, throbbing, aching, etc.) and typically leading to an evasive action by the individual. As used herein, the term pain also includes chronic and acute neuropathic pain. The term "chronic neuropathic pain" refers to a complex, chronic pain state that is usually accompanied by tissue injury wherein the nerve fibers themselves may be damaged, dysfunctional or injured. These damaged nerve fibers send incorrect signals to other pain centers. The impact of nerve fiber injury includes a change in nerve function both at the site of injury and areas around the injury. The term "acute neuropathic pain" refers to self-limiting pain that serves a protective biological function by acting as a warning of on-going tissue damage. Acute neuropathic pain is typically a symptom of a disease process experienced in or around the injured or diseased tissue.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (e.g., a monkey, such as a cynomolgus or rhesus monkey, chimpanzee, etc.) and a human). In some embodiments, the subject may be a human or a non-human. In one embodiment, the subject is a human. The subject or patient may be undergoing various forms of treatment.

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a treatment to a subject that is not at the time of administration afflicted with the disease. "Preventing" also refers to preventing the recurrence of a disease or of one or more symptoms associated with such disease.

"Therapy" and/or "therapy regimen" generally refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. In some embodiments, the treatment comprises the treatment, alleviation, and/or lessening of pain.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, neurobiology, microbiology, genetics, electrical stimulation, neural stimulation, neural modulation, and neural prosthesis described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. OPTIMIZED SCS PATTERNS

Figure 1:
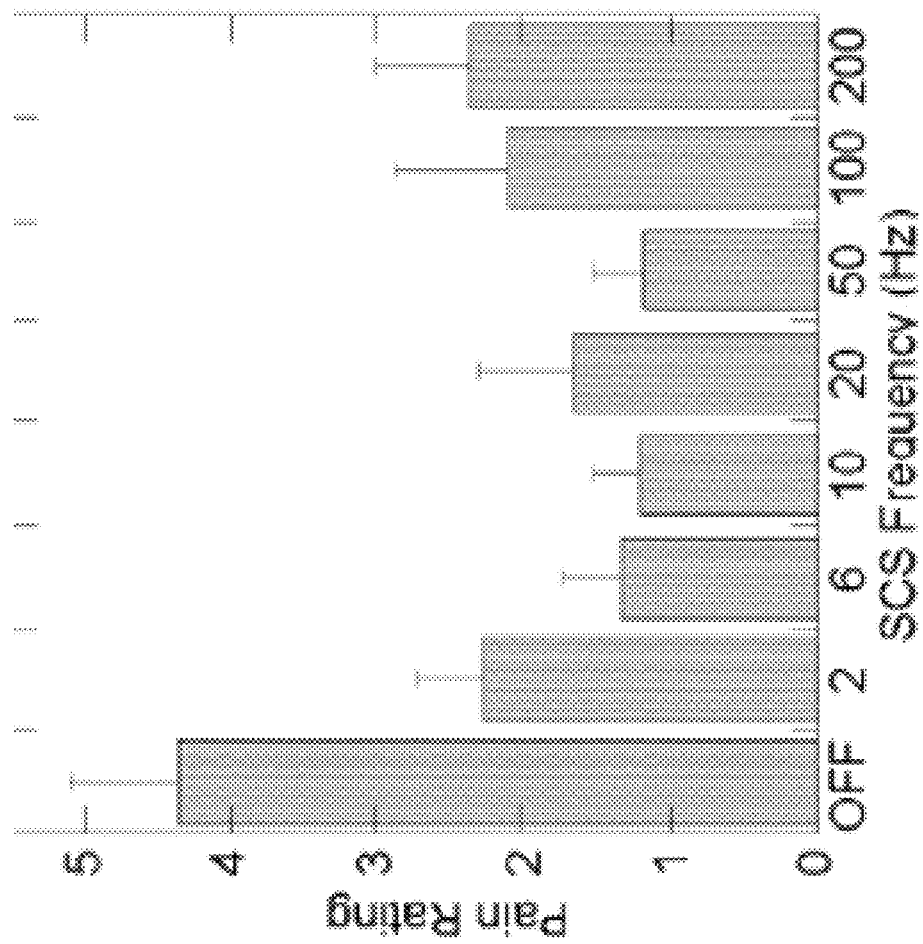
FIG. 1 includes representative results of patient pain rating scores during SCS treatment showing a significant degree of variability (Mean+SEM; n=5).

Embodiments of the present disclosure provide methods for designing optimized temporal patterns of stimulation to minimize the variance of patient responses to SCS (see, e.g., FIG. 1). This variance includes, for example, patient-to-patient response variability, as well as variance over time within a particular patient. In some embodiments, the methods include the use of a validated computational model of SCS to design optimized patterns of SCS using a fitness function to evaluate the fitness of the SCS patterns. This design method and the resulting temporal patterns of stimulation will provide various advantages, including but not limited to, improved clinical efficacy and simplified neuromodulation device programming.

In some embodiments, the methods include the use of a computational model of the effects of SCS on spinal cord pain networks. For example, computational models indicated that the activity of wide dynamic range (WDR) neurons that transmit pain signals to the brain is strongly dependent on the pulse repetition frequency of SCS (see, e.g., FIG. 2). The firing rate of model WDR neurons is generally considered a validated proxy for the level of pain (e.g., neuropathic pain), as there is a significant correlation between firing rate of model WDR neurons and pain ratings, and changes in WDR firing rates during SCS parallel behavioral effects on pain.

Network changes in the spinal cord, such as a reduction of inhibition, changes in intrinsic plasticity, and abnormal functioning of afferents influence pain sensations. The computational models provided herein incorporate representations of these network changes to represent variability in pain state. For example, loss of function of KCC2 Cl$^-$ transporters can lead to a depolarizing shift in anionic reversal potentials in the local network. Additionally, loss of GABAergic inhibition decreases the weight of afferent inputs onto inhibitory interneurons and from inhibitory interneurons to WDR neurons in local and surround networks. And spreading pain increases the number of small diameter (C-fiber) afferents with ectopic activity in surround networks.

In accordance with embodiments of the present disclosure, variance in pain states were simulated (within and across patients) by changing the weighted input levels of the model variants across a large number of simulations (see, e.g., FIGS. 4A-4D). This can be accomplished, for example, with Latin hypercube Monte Carlo sampling or Design of Experiments approaches, or other suitable methods. Applying different SCS frequencies to different modeled pain states indicated that there is significant variability in the model output, and it is this variability across the changes in model parameters that represents the pain variance within and across patients. Furthermore, this variability is at least partially dependent on the stimulation frequency, indicating that changing stimulation parameters can be a useful way of determining the amount of variability in patient responses.

The systems and methods provided herein introduce novel means for designing and evaluating optimized temporal patterns of SCS to reduce the variability in response to SCS across pain states within a patient and between patients, and in a plurality of patients with different pain states, which increases clinical efficacy and simplifies neuromodulation device programming. In some cases, pain states can refer to the pain experienced by different patients with the same disease etiology (e.g., source of neuropathic pain), and/or the pain experienced by different patients with different disease etiologies, and/or the pain experienced by a single patient as his/her condition improves, worsens, or changes. The methods provided herein include the use of an optimization algorithm (e.g., genetic algorithm, particle swarm optimization, simulated annealing) to design temporal patterns of stimulation to reduce the variance of the changes in firing in a neuron in the computation model (see, e.g., FIG. 6). For example, a pattern could be designed to reduce the firing rate of the WDR neuron, and thereby reduce pain. The methods further provide for the identification of temporal patterns to reduce the variance of the reduction of neural firing rate, such that the resulting pattern produces robust reductions in pain across disease conditions and clinical indications.

In some embodiments, generating a SCS pattern having an optimized temporal pattern of stimulation is performed using an optimization algorithm, such as a genetic algorithm. A genetic algorithm uses natural selection as a basis for solving optimization problems. Although various embodiments described herein are based on the use of a genetic algorithm, other optimization algorithms may be employed in a computational model of neural stimulation. Other optimization algorithms that may be used include, for example, simulated annealing, Monte-Carlo methods, other evolutionary algorithms (e.g., genetic algorithm, evolutionary programming, genetic programming), swarm algorithms (e.g., ant colony optimization, bees optimization), differential evolution, firefly algorithm, invasive weed optimization, harmony search algorithm, and/or intelligent water drops. Additionally, as would be recognized by one of ordinary skill in the art based on the present disclosure, other optimization methods and algorithms can also be used in conjunction with the methods and systems designed herein.

In accordance with these embodiments, the computation model receives a temporal pattern of stimulation as an input. The fitness of the temporal pattern was evaluated using a fitness function based on three factors: the reduction in pain score in the model (where the pain score is related to a change in firing rate and or pattern of one or more neurons in the model), the efficiency of the pattern (where the efficiency is proportional to the average frequency of stimulation and is important for evaluating the impact on battery life or recharge interval of implantable pulse generations), and the variance of the reduction of pain scores across different pain models (where the reduction in variance in model responses corresponds to a reduction of within or across patient variability in the response to SCS). The genetic algorithm designs new temporal patterns based on the patterns that received the highest fitness scores in the previous round. The process repeats until the algorithm has converged on an optimal or optimized solution.

In some embodiments, each term in the fitness function of the optimization algorithm has a weighting coefficient, which allows for the control of how much each of the factors will influence pattern design or selection. Optimization algorithm applications have previously used fitness functions that optimize for performance and efficiency. However, embodiments of the present disclosure include methods that introduce variance reduction in pain states as a new term to the fitness function to improve clinical efficacy.

In accordance with these embodiments, and as exemplified in FIGS. 7 and 8, optimized SCS patterns can include a temporal pattern of electrical stimulation pulses, and/or the temporal pattern of electrical stimulation pulses can include a non-regular temporal pattern with one or more varying inter-pulse intervals. In some embodiments, the pattern of electrical stimulation may be applied at multiple different frequencies and at different timings. Further, the patterns may be applied at different frequencies that are multiples of each other. The pattern of electrical stimulation may include regular temporal patterns of stimulation (e.g., constant inter-pulse intervals) or non-regular temporal patterns of stimulation (e.g., interpulse intervals that vary in time). In some embodiments, the optimized SCS pattern comprises a stimulation frequency ranging from about 1 Hz to about 200 Hz, from about 1 Hz to about 175 Hz, from about 1 Hz to about 150 Hz, from about 1 Hz to about 125 Hz, from about 1 Hz to about 100 Hz, from about 1 Hz to about 75 Hz, from about 1 Hz to about 50 Hz, from about 50 Hz to about 150 Hz, from about 50 Hz to about 100 Hz, and from about 100 Hz to about 200 Hz.

3. METHODS AND SYSTEMS

Embodiments of the present disclosure include a method of identifying an optimized spinal cord simulation (SCS) pattern for pain reduction. In accordance with these embodiments, the method includes generating a plurality of SCS patterns using an optimization algorithm based on predetermined performance criteria. In some embodiments, the plurality of SCS patterns can be generated for at least one of efficiency optimization, efficacy optimization, and variance optimization.

Figures 2A, 2B, 2C, 2D:
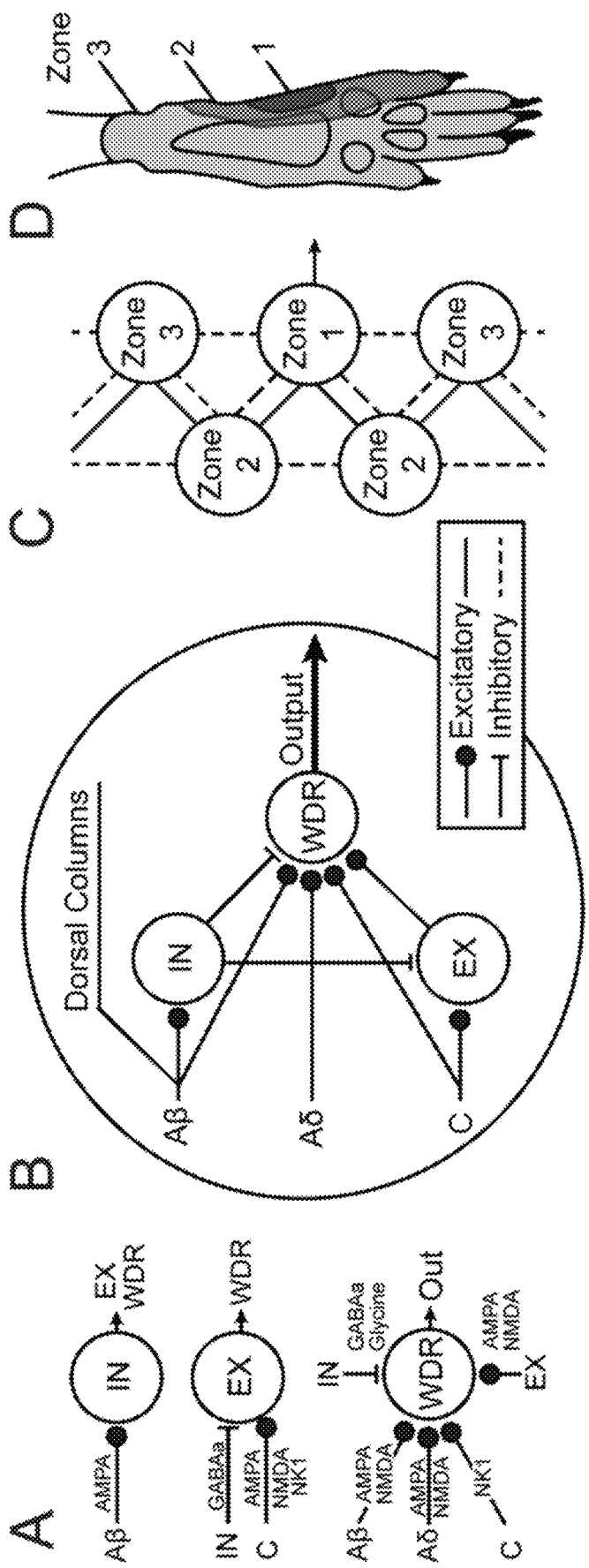
FIGS. 2A-2D depicts representative architecture of a distributed biophysical network model of the dorsal horn and model responses to spinal cord stimulation.
Figure 2E:
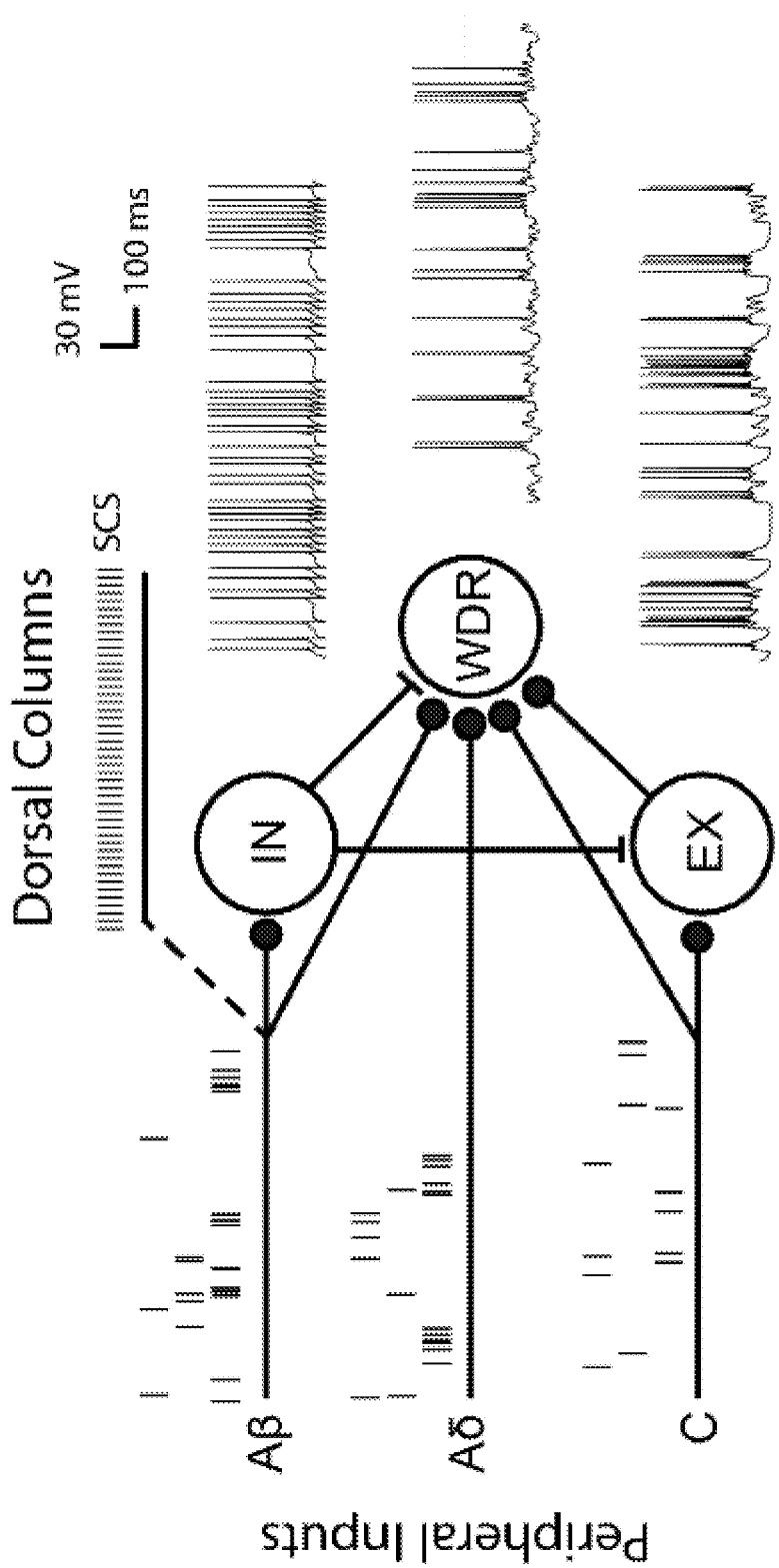
FIG. 2E: Default model inputs and outputs in neuropathic pain condition for Zone 1 model neurons. Example spike trains for primary afferent fibers (15 Aβ, 15 Aδ, and 30 C) carrying ectopic activity to the center neurons. One third of Aβ and Aδ fibers exhibit bursting behavior (bottom spike trains). The voltage traces of the output neurons are shown on the right. Scale bar, 100 ms and 30 mV.
Figure 2F:
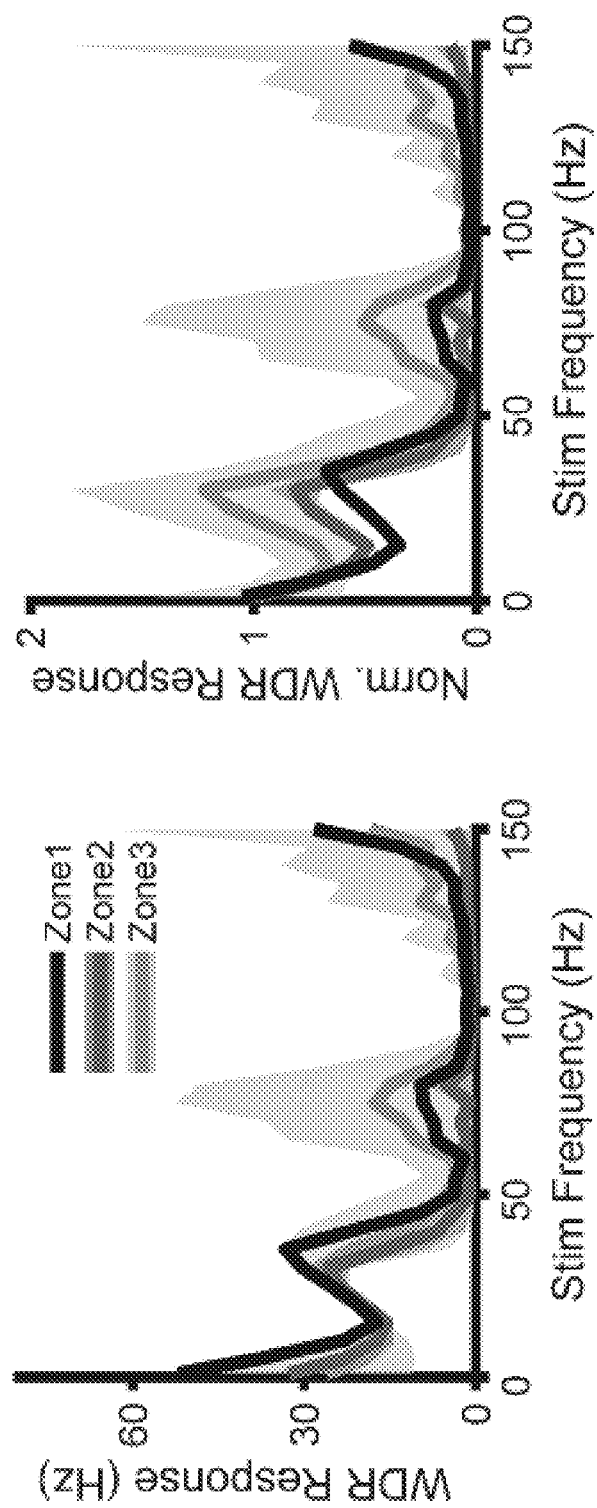
FIG. 2F: Response of WDR neurons in each Zone from 1-150 Hz for the default network state. Traces represent the average response over 10 trials. The shaded region represents the average minimum and maximum response for Zone 2 and Zone 3 across 10 trials. Left, raw modeled WDR responses. Right, modeled WDR responses normalized to the baseline firing rate in each simulation.

In some embodiments, the optimization algorithm is a genetic algorithm, a particle swarm algorithm, a simulated annealing algorithm, an ant colony algorithm, an estimation of distribution algorithm, and any combinations and derivations thereof (see, e.g., FIG. 6). In accordance with these embodiments, the method can include an algorithm that controls the delivery of multiple frequencies of SCS through different output channels to different contacts on a SCS electrode (FIG. 2).

Evaluating the SCS patterns can occur using, for example, a genetic algorithm in which optimal stimulation patterns are developed and evaluated over several iterations, or "generations." In some embodiments, the genetic algorithm evaluates SCS patterns across about 50 to about 150 generations. In some embodiments, the first generation includes 25 randomly generated patterns, each containing about 1000 "bits" representing 1 millisecond bins during which an SCS pulse may be delivered over a given 1 second interval; the overall SCS pulse train during the 5-second stimulation period can be built from 5 successive repeats of a given pattern. Optimization methods in accordance with these embodiments can be used to design or identify unique temporal patterns of SCS that are more effective at suppressing model WDR neuron behavior versus equivalent regular frequency stimulation through testing of the prototype algorithm using a computational model of pain.

In some embodiments, the computational model of the neuronal network is coupled to the optimization algorithm by the predetermined performance criteria. For example, the algorithm may use the output of model WDR projections neurons responsible for transmitting nociceptive information to the brain to optimize the temporal pattern of stimulation delivered during SCS such that stimulation suppresses the activity of these WDR neurons as much as possible and at the lowest possible frequency. In some embodiments, the computational model shown in FIG. 2E may be utilized. In some embodiments, the predetermined performance criteria can be incorporated into a fitness function used to evaluate the fitness of the plurality of SCS patterns. The predetermined performance criteria can include at least one of a reduction in pain score (e.g., efficacy of reducing WDR activity), SCS pattern efficiency (e.g., reducing stimulation frequency), and variance of pain score reduction across different pain states. The relative significance of these performance criteria can be controlled by modifying a weighting coefficient to generate a family of temporally optimized stimulation patterns.

In some embodiments, the reduction in the pain score includes a change in firing rate and/or firing pattern of one or more neurons in the computational model. In some embodiments, the SCS pattern efficiency is proportional to the average frequency of stimulation. And in some embodiments, the variance of pain score reduction across different pain states corresponds to variance of the response to SCS across a population of computational models of a neuronal network. The response to SCS can also include a change in firing rate and/or firing pattern of one or more neurons in the computational model.

4. COMPUTATIONAL MODELS

Figure 3:
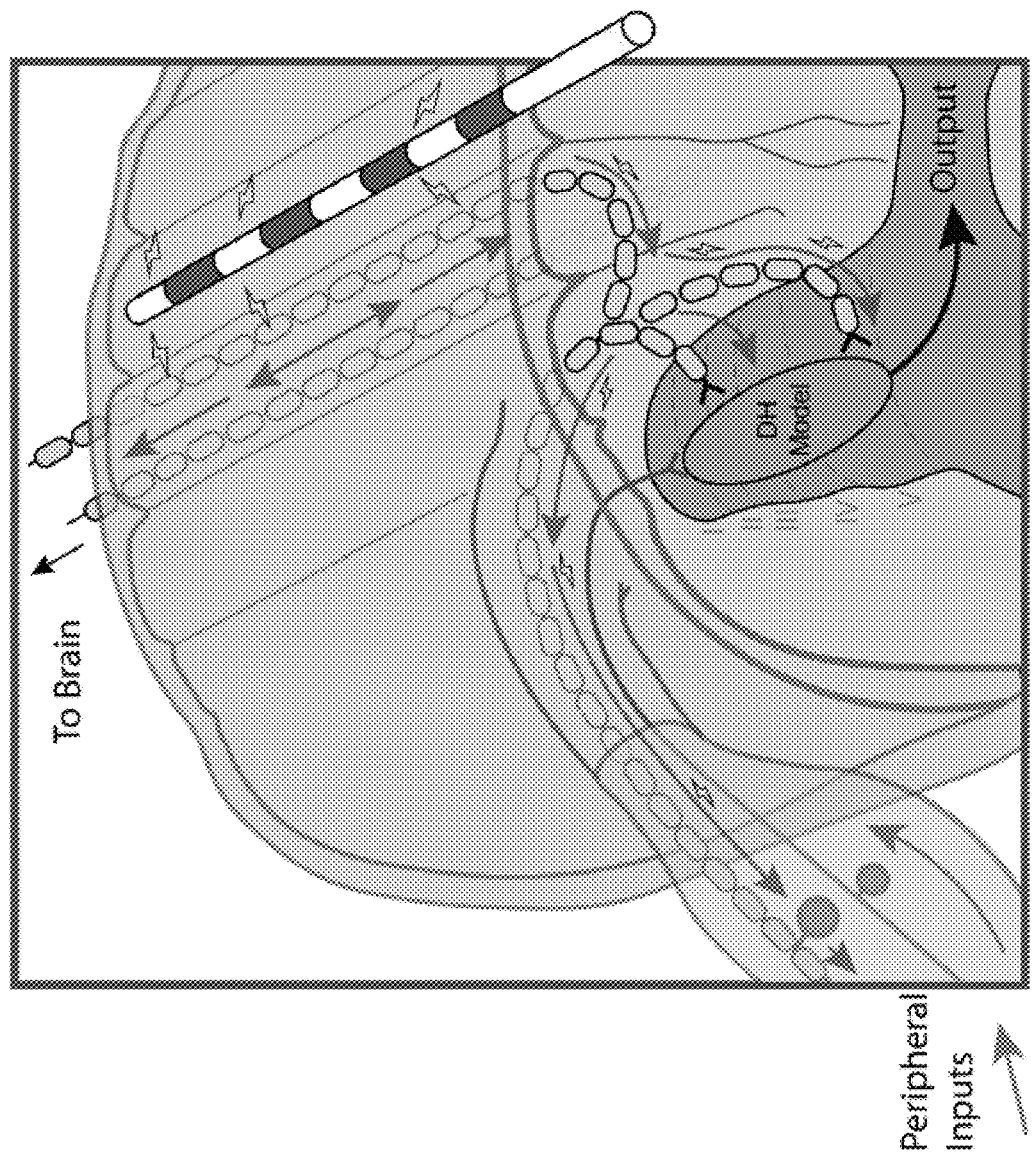
FIG. 3 includes a representative illustration of the biological basis for the biophysical model of the dorsal horn network provided herein.
Figures 4A, 4B, 4C, 4D:
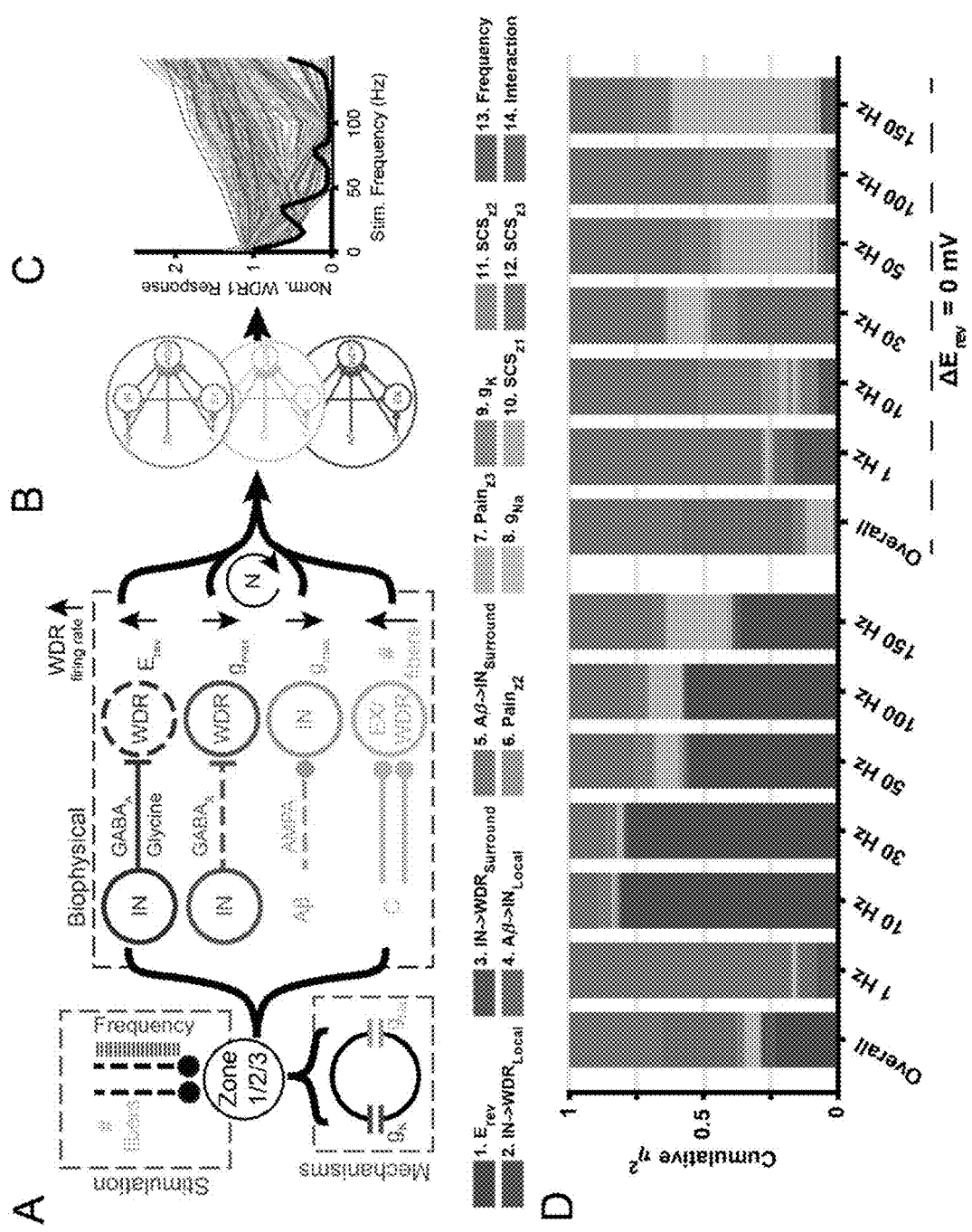
FIG. 4A: Inputs to the model that were varied in simulations. Stimulation parameters include the number of fibers activated by SCS and stimulation frequency in each zone. Mechanism parameters include the sodium and potassium conductance. Biophysical parameters include the reversal potential of the inhibitory synapses, maximum conductance of GABAergic synapses, maximum conductance of AMPA synapses onto IN interneurons, and the number of C fibers activated in surround Zones. Grey represents the actual parameter that is changing, and the numbers correspond to parameter numbers in FIG. 4D. (See Table 1 for a more detailed description of each parameter.)
FIG. 4B: Demonstrates that changes in the input parameters generated 2000 different network states.
FIG. 4C: Representative responses of 500 network states versus stimulation input frequencies between 1 and 150 Hz. All responses are normalized to the baseline response with no SCS input.
FIG. 4D: Quantifies the effect size of various parameters on the variance of the firing rate of the WDR neuron in zone 1 using $\eta^2$. The proportion of the bar represents the magnitude of the effect of each parameter across all simulations and at particular frequencies of interest. The parameters are sorted by color according to Table 1. The analysis is repeated (labeled $\Delta\ E_{rev}$=0 mV) excluding model states with changing reversal potential because the effect of reversal potential dominated at some frequencies.
Figure 5:
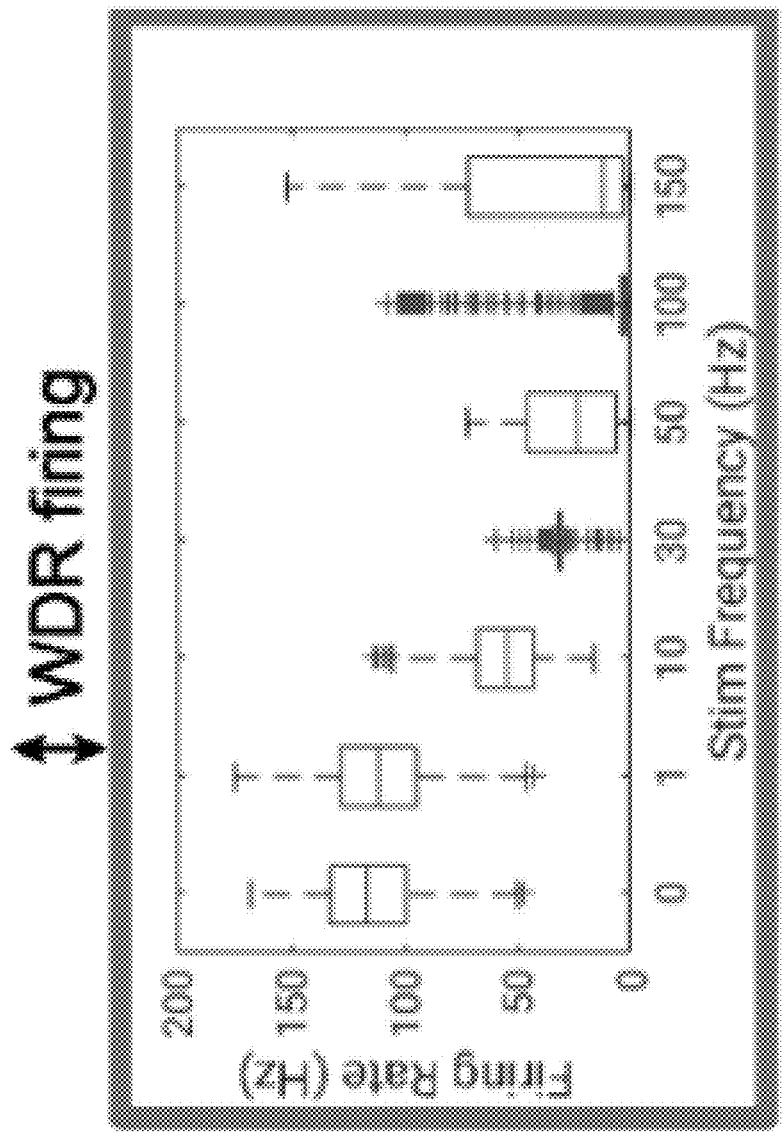
FIG. 5 includes a representative box plot of the range of outputs generated from changing the inputs of the model. Red lines indicate medians, box edges demarcate the $25^{th}$ and $75^{th}$ percentiles, dotted line edges indicate +/−2.7σ for a normally distributed data set, and red crosses indicate outliers.

Embodiments of the systems and methods of the present disclosure also include evaluating a plurality of SCS patterns for pain reduction using a computational model of a neuronal network, such as a computational network model of the dorsal horn described above (see, e.g., FIG. 3). In some embodiments, the methods include determining one or more of the non-regular temporal patterns that results in predetermined WDR neuronal output and stimulation activity. Predetermined WDR neuronal output may include, but is not limited to, the output of a model WDR neuron in a simulation implemented in a computational model, which has inputs for modeling a biological WDR neuron. In this sense, the model WDR neuron's output can be used as a proxy for patient pain (i.e. efficacy).

In one example, a computing device can be used to generate and utilize a cost function for optimizing the WDR neuronal output and stimulation activity. Further, the computing device can select one or more of the non-regular temporal patterns based on the cost function. Further, the computing device can alter the temporal patterns and determine when a threshold value for the cost function is obtained while altering the temporal patterns. Additionally, the computing device can determine that the temporal pattern applied when the threshold value is obtained is the non-regular temporal pattern(s) that results in predetermined WDR neuronal output and stimulation activity. This temporal pattern may be determined to be the temporal pattern that provides the lowest WDR neuronal output, and/or the lowest stimulation activity, and/or the highest variance reduction among all other applied temporal patterns. As referred to herein, the term "efficacy" refers to the minimization of model WDR activity (proxy for reduced pain); the term "efficiency" refers to a low or the lowest possible device stimulation frequency (power savings); and the term "variance reduction" refers to variance in the response to SCS across a population of computational models of a neuronal network.

In some embodiments, the computational model of the neuronal network simulates activity of a WDR neuron, which is used as a proxy for pain. As shown in FIGS. 2A-2D, the computational model of the neural network can include three network zones comprising heterogeneous inhibitory and excitatory neural connections. In accordance with these embodiments, the computational model of the neural network can simulate a network state by varying at least one of: a biophysical input parameter, a stimulation input parameter, and a mechanism input parameter.

In some embodiments, the biophysical input parameter can include: i) reversal potential of inhibitory synapses within each network zone; ii) maximum conductance of GABAergic synapses within each network zone; iii) maximum conductance of AMPA synapses onto inhibitory neurons within each network zone; and iv) number of C fibers activated in each surround zone. The reverse potential of inhibitory synapses can range from about −50 mV to about −100 mV; the maximum conductance of GABAergic synapses can range from about 50% to about 100%; the maximum conductance of AMPA synapses onto inhibitory neurons can range from about 50% to about 100%; and the number of C fibers activated in each surround zone can range from about 0% to about 50%.

In some embodiments, the computational model can simulate a response to an SCS pattern by varying the at least one stimulation input parameter. In accordance with these embodiments, the at least one stimulation input parameter can include: i) number of fibers activated within each network zone by an SCS pattern; and ii) stimulation frequency of an SCS pattern within each network zone. The number of fibers activated within each network zone by the SCS pattern can range from about 0% to about 100% in a first network zone, from about 0% to about 100% in a second network zone, and from about 0% to about 100% in a third network zone. The stimulation frequency within each network zone can range from about 1 Hz to about 200 Hz, from about 1 Hz to about 175 Hz, from about 1 Hz to about 150 Hz, from about 1 Hz to about 125 Hz, from about 1 Hz to about 100 Hz, from about 1 Hz to about 75 Hz, from about 1 Hz to about 50 Hz, from about 50 Hz to about 150 Hz, from about 50 Hz to about 100 Hz, and from about 100 Hz to about 200 Hz.

In some embodiments, the computational model can simulate a response to an SCS pattern by varying the at least one mechanism input parameter. In accordance with these embodiments, the at least one mechanism input parameter can include: i) maximum sodium conductance; and ii) maximum potassium conductance. The maximum sodium conductance can range from about 50% to about 150% within a network zone, and the maximum potassium conductance can range from about 50% to about 150% within a network zone.

5. SCS DELIVERY SYSTEMS AND METHODS

Notwithstanding the embodiments described herein, the methods and systems for administering SCS based on temporal patterns of stimulation described in U.S. patent application Ser. Nos. 14/774,156, 14/774,160, and 15/806,686 are herein incorporated by reference in their entireties and for all purposes.

Additionally, SCS delivery systems and methods of the present disclosure include a system for delivering spinal cord stimulation to a subject in order to reduce, treat, or prevent the subject's neuropathic pain. In accordance with these embodiments, the system includes an electrode sized and configured for implantation in proximity to neural tissue. For example, the system can include an SCS device, an electrical connection lead, and at least one electrode or electrode array operatively positioned in the epidural space of a vertebral column of a subject that is experiencing neuropathic pain. The electrode or electrode array can be positioned at the site of nerves that are the target of stimulation (e.g., along the spinal cord), or positioned in any suitable location that allows for the delivery of electrical stimulation to the targeted neural tissue.

In some embodiments, the system includes a pulse generator coupled to the electrode. The pulse generator can include a power source comprising a battery and a microprocessor coupled to the battery, and the pulse generator is generally configured to generate electrical signals for delivering an SCS pattern having an optimized temporal pattern of electrical stimulation capable of reducing pain. In some embodiments, the system further includes a controller comprising hardware, software, firmware, or combinations thereof for implementing functionality described herein. For example, the controller can be implemented by one or more processors and memory. The controller can be operatively connected to the pulse generator to facilitate the generation of electrical signals and applying temporal patterns of electrical stimulation to targeted neurological tissue. The output signals may be received by the connection lead and carried to the electrode or electrode array for the delivery of electrical stimulation to targeted neurological tissue. The system can include a power source, such as a battery, for supplying power to the controller and the pulse generator.

Embodiments of the present also include methods for delivering spinal cord stimulation to reduce pain using the systems described herein. In accordance with these embodiments, the method includes programming the pulse generator to output the optimized SCS pattern and delivering the SCS pattern to a subject to reduce pain. In some embodiments, the optimized SCS pattern reduces pain in a plurality of subjects with different pain states. In some embodiments, the optimized SCS pattern includes non-regular temporal patterns with one or more varying inter-pulse intervals. And in some embodiments, delivering an optimized SCS pattern to a subject includes delivering one or more different SCS patterns to one or more different neuronal populations.

In some embodiments, the system also includes an external computing device that is not implanted within the subject. The computing device can communicate with an SCS device or system via any suitable communication link (e.g., a wired, wireless, or optical communication link). The communication link may also facility battery recharge. A clinician may interact with a user interface of the computing device for programming the output of the implanted pulse generator, including the electrodes that are active, the stimulation pulse amplitude, the stimulation pulse duration, the stimulation pattern (including pulse repetition frequency), and the like applied via each electrode contact to each sub-population. In accordance with these embodiments, systems and methods of the present disclosure can be used to deliver optimized SCS patterns, as described herein, to reduce pain in a plurality of subjects with different pain states. The optimized SCS pattern can include non-regular temporal patterns with one or more varying inter-pulse intervals. In some embodiments, delivering an SCS pattern having an optimized temporal pattern of electrical stimulation includes delivering one or more SCS patterns to one or more electrodes.

In some embodiments, systems and methods of the present disclosure can be implemented as an algorithm within a SCS pulse generator device. An on-board controller can deliver multiple frequencies and patterns of SCS through different output channels to different contacts on the spinal cord stimulation electrode. By virtue of stimulation through multiple contacts, different populations of axons (e.g., sub-populations of dorsal column nerve fibers) traversing the dorsal column may be activated at different frequencies and in different patterns, resulting in greater suppression of the neurons responsible for transmitting nociceptive information to the brain. Values of the stimulation frequencies and patterns of stimulation and the electrodes through which these frequencies and patterns are delivered can be input by either a physician or a patient through a user interface. Alternatively, the device can be pre-programmed with specific combinations of frequencies and patterns to use. The applied frequencies and patterns may or may not be offset from each other at the start of stimulation. In addition, the delivered frequencies and patterns of SCS may be limited to 2 frequencies and patterns, as many frequencies and patterns and axon populations as the stimulation technology will allow can be delivered to the patient. The algorithm can be toggled on and off (e.g., between multi-frequency and single frequency SCS) by either the physician or patient, or it can be coupled to an internal feedback-driven algorithm for automatic control.

In some embodiments, computer readable program instructions for carrying out operations of the present disclosure, including programming the pulse generator to output the optimized SCS pattern, can be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

6. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Network Architecture and Biophysics.

A biophysically-based computational network model of the dorsal horn was used as the basis for the distributed network model described herein. The model includes the use of primary afferent fibers that conveyed information from the peripheral receptive field to the model neurons that represented central sensory processing within the dorsal horn. Peripheral spatiotemporal inputs to the model were conveyed through three types of primary afferents: large diameter afferents (Aβ) convey touch information, while smaller thinly myelinated (Aδ) and unmyelinated (C) afferents convey nociceptive information. The afferent fibers communicated information through spikes drawn from a homogeneous Poisson process representing biological spike rates with delays drawn from conduction velocities provided in previous studies. SCS inputs were applied through Aβ fibers. Since SCS inputs are assumed to propagate antidromically from the stimulation site to the network, a 100-mm distance between the stimulation site and the network was assumed, and a spike collision model between orthodromic peripheral inputs and SCS inputs was implemented. The network used three types of model neurons: inhibitory (IN) interneurons, excitatory (EX) interneurons, and wide-dynamic range (WDR) projection neurons. The synaptic connections within the model were based on the previous model with some modifications to represent the expanded network architecture, as shown in FIG. 2A.

The network architecture of the model was multilayered with individual nodes representing processing within different zones and inhibitory and/or excitatory connections between nodes representing connections across the entire receptive field. The connections within each node (FIG. 2B) were based on the gate control theory and computational models of the dorsal horn. Model IN interneurons received inputs from Aβ fibers, EX interneurons received inputs from C fibers and the IN interneuron, and WDR projection neuron received inputs from Aβ, Aδ, and C fibers, as well as IN and EX interneurons. The connections between zones (FIG. 2C) were based on experimental recordings of surround inhibition showing three distinct zones. Zone 1 receives information from primary afferents in the center of the receptive field, zone 2 from the area immediately surrounding zone 1, and zone 3 from the peripheral areas of the receptive field (FIG. 2D). Zone 2 sends both inhibitory and high threshold excitatory inputs to zone 1. Inhibition from zone 2 increases the focality for painful stimuli while the high-threshold excitatory inputs increase the magnitude of signals for larger stimuli. Zone 3 and sends only inhibitory inputs to zone 1.

Inhibitory connections between zones were from the surround IN interneuron to the local EX interneuron and local WDR projections neuron. Excitatory connections between zones were from the surround EX neuron to the local WDR projection neuron. As disclosed herein, surround EX or IN neuron generally refers to an excitatory or inhibitory neuron that receives peripheral inputs from the surround area of the center of the receptive field. Note that the connections were bidirectional because the surround of the zone 1 receptive field area is the center of another receptive field area. Therefore zone 1 also sent inhibitory connections to zone 2 and zone 3 nodes. The weight of the connections was modified from the weight of surround inhibition, so that the baseline firing rate of the zone 1 WDR neuron in the default network state did not change. The total conductance of inhibitory synapses from local IN to local WDR was about 5.3 nS for both glycinergic and GABAergic connections. The total conductance of GABAergic inhibition was about 5.8 nS for surround IN to local WDR synapses and about 7.3 nS for surround IN to local EX synapses. The total conductance of AMPA connections was about 2.2 nS for local EX to local WDR synapses and about 1.5 nS for surround EX to local WDR synapses.

The total conductance of synapses between primary afferents and model neurons was the same as in previous studies (e.g., Zhang et al. (2014b)). The membrane dynamics of the individual neurons and model neuron geometry were also unchanged. Briefly, neuron dynamics are based on patch-clamp recordings from substantia gelatinosa and deep dorsal horn neurons. Each neuron is a Hodgkin-Huxley type membrane model with four segments—a dendrite, soma, axon initial segment (hillock), and axon. The ionic currents in each component of the neuron and the compartment sizes match previous studies. All simulations were conducted in the NEURON simulation environment (v7.4 and v7.5).

Example 2

Network Model Variation.

The Monte Carlo method relies on repeated random sampling of inputs to compute results for uncertain scenarios. In the present disclosure, random network states were generated by varying several parameters in three categories: stimulation, mechanisms, and biophysical parameters. Stimulation parameters represented possible changes to the SCS program through the spatial complement of fibers that was activated or by modifying the frequency. Mechanism parameters represented random differences in the conductances of projection neurons that change excitability. Biophysical parameters represented the changes in network states that occur due to progression of neuropathic pain and loss of inhibition in the network. Table 1, below, includes a description of each parameter and the constraints used for the Monte Carlo simulations.

TABLE 1

Inputs for Monte Carlo simulations (constraints for the parameters representing pain in the model).

| Input Names | Range (units) | Description |
| --- | --- | --- |
| Stimulation | | |
| Frequency | 1, 10, 30, 50, 100, 150 (Hz) | SCS stimulation frequency |
| $SCS_{Z1}$ | 50 ↔ 100 (%) | Proportion of Aβ fibers activated in zone 1 by SCS input |
| $SCS_{Z2}$ | 0 ↔ 100 (%) | Proportion of Aβ fibers activated in zone 2 by SCS input |
| $SCS_{Z3}$ | 0 ↔ 100 (%) | Proportion of Aβ fibers activated in zone 3 by SCS input |
| Mechanism | | |
| $g_{Na}$ | 50 ↔ 150 (%) | Maximum sodium conductance for zone 1 WDR neuron |
| $g_K$ | 50 ↔ 150 (%) | Maximum potassium conductance for zone 1 WDR neuron |
| Biophysical | | |
| $E_{rev}$ | −70, −66, −62, −58, −54 (mV) | Shift in anionic reversal potentials due to loss of function of the Cl⁻ transporter KCC2 |
| Aβ → $IN_{Local}$ | 50 ↔ 100 (%) | Change in conductance of Aβ fiber inputs to local inhibitory interneuron |
| Aβ → $IN_{Surround}$ | 50 ↔ 100 (%) | Change in conductance of Aβ fiber inputs to surround inhibitory interneuron |
| IN → $WDR_{Local}$ | 50 ↔ 100 (%) | Change in GABAergic conductance from local inhibitory interneuron (IN) to local WDR neuron |
| In → $WDR_{Surround}$ | 50 ↔ 100 (%) | Change in GABAergic conductance from surround inhibitory interneurons (IN) to local WDR neuron |
| $Pain_{z2}$ | 0 ↔ 50 (%) | Activation of small diameter (Aδ & C) fibers in zone 2 |
| $Pain_{z3}$ | 0 ↔ 50 (%) | Activation of small diameter (Aδ & C) fibers in zone 3 |

Random network states were generated with latin hypercube sampling (LHS) of input parameters (except frequency). LHS generates a square grid of M intervals for N variables within the range for each parameter where M is the number of trials. LHS ensures that the random sample is a sufficient representation of the variability within the parameter. Each network state was tested at 1, 10, 30, 50, 100, and 150 Hz because these frequencies were identified as important inflection points.

Example 3

Genetic Algorithm.

This example provides a representative method of identifying an optimized SCS pattern for pain reduction using a genetic algorithm. FIGS. 7A-7C show the performance of the best pattern across nine different network states and twenty-five generations. In particular, FIG. 7A includes a representation of multiple network states, while FIG. 7B includes a representative graph (boxplots) showing the range of performance scores across network states for the best temporal pattern of SCS as the algorithm evolves. Decreasing scores as indicated by the placement of the bar along the y-axis in the plot represent increases in the efficacy of the patterns while reductions in the range of scores decreases the variance in efficacy across states. FIG. 7C includes examples of the top five performing 1000 ms long temporal patterns of SCS evolving between the $1^{st}$ and $25^{th}$ generation of the genetic algorithm. An optimization algorithm typically runs for at least 25 generations and may run longer.

FIGS. 8A-8C show the performance of the best pattern across nine different network states and fifty generations with different relative weightings of the fitness function than in FIGS. 7A-7C. In particular, FIG. 8A includes a representation of multiple network states, while FIG. 8B includes a representative graph (boxplots) showing the range of performance scores across network states for the best temporal pattern of SCS as the algorithm evolves. Decreasing scores as indicated by the placement of the bar along the y-axis in the plot represent increases in the efficacy of the patterns while reductions in the range of scores decreases the variance in efficacy across states. FIG. 7C includes examples of the patterns for the 1st and 25th generation of the genetic algorithm. FIG. 8C includes examples of the top five performing 1000 ms long temporal patterns of SCS evolving between the $1^{st}$ and $50^{th}$ generation of the genetic algorithm. An optimization algorithm typically runs for at least 25 generations and may run longer.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

For reasons of completeness, various aspects of the disclosure are set out in the following numbered clauses:

Clause 1. A method of identifying an optimized spinal cord simulation (SCS) pattern for pain reduction, the method comprising: generating a plurality of SCS patterns using an optimization algorithm based on predetermined performance criteria; evaluating the plurality of SCS patterns for pain reduction using a computational model of a neuronal network; and identifying at least one candidate SCS pattern having an optimized temporal pattern of stimulation capable of reducing pain.

Clause 2. The method according to clause 1, wherein the plurality of SCS patterns are generated for at least one of efficiency optimization, efficacy optimization, and variance optimization.

Clause 3. The method according to clause 1 or clause 2, wherein the optimized SCS pattern reduces pain in a plurality of subjects with different pain states.

Clause 4. The method according to any of clauses 1 to 3, wherein the optimized SCS pattern comprises a temporal pattern of electrical stimulation pulses.

Clause 5. The method according to clause 4, wherein the temporal pattern of electrical stimulation pulses comprises a non-regular temporal pattern with one or more varying inter-pulse intervals.

Clause 6. The method according to clause 4, wherein the optimized SCS pattern comprises a stimulation frequency ranging from about 1 Hz to about 200 Hz.

Clause 7. The method according to any of clauses 1 to 6, wherein the optimization algorithm comprises at least one of a genetic algorithm, a particle swarm algorithm, a simulated annealing algorithm, an ant colony algorithm, an estimation of distribution algorithm, a gradient descent algorithm, and any combinations and derivations thereof.

Clause 8. The method according to any of clauses 1 to 7, wherein the predetermined performance criteria are incorporated into a fitness function used to evaluate the fitness of the plurality of SCS patterns.

Clause 9. The method according to any of clauses 1 to 7, wherein the predetermined performance criteria comprise at least one of: i) reduction in pain score; ii) SCS pattern efficiency; and iii) variance of pain score reduction across different pain states.

Clause 10. The method according to clause 9, wherein the reduction in the pain score comprises a change in firing rate and/or firing pattern of one or more neurons in the computational model.

Clause 11. The method according to clause 9, wherein the SCS pattern efficiency is proportional to the average frequency of stimulation.

Clause 12. The method according to clause 9, wherein the variance of pain score reduction across different pain states corresponds to variance of the response to SCS across a population of computational models of a neuronal network.

Clause 13. The method according to clause 12, wherein the response to SCS comprises a change in firing rate and/or firing pattern of one or more neurons in the computational model.

Clause 14. The method according to any of clauses 1 to 13, wherein the computational model of the neuronal network is coupled to the optimization algorithm by the predetermined performance criteria.

Clause 15. The method according to any of clauses 1 to 14, wherein the computational model of the neuronal network simulates activity of a wide dynamic range (WDR) neuron.

Clause 16. The method according to clause 15, wherein the activity of the WDR neuron in the computational model is a proxy for pain.

Clause 17. The method according to any of clauses 1 to 16, wherein the computational model of the neural network comprises three network zones comprising heterogeneous inhibitory and excitatory neural connections.

Clause 18. The method according to any of clauses 1 to 17, wherein the computational model of the neural network simulates a network state by varying at least one of: a biophysical input parameter, a stimulation input parameter, and a mechanism input parameter.

Clause 19. The method according to clause 18, wherein the computational model simulates a pain state of a subject by varying the at least one biophysical input parameter, and wherein the at least one biophysical input parameter comprises: i) reversal potential of inhibitory synapses within each network zone; ii) maximum conductance of GABAergic synapses within each network zone; iii) maximum conductance of AMPA synapses onto inhibitory neurons within each network zone; and iv) number of C fibers activated in each surround zone.

Clause 20. The method according to clause 19, wherein the reversal potential of inhibitory synapses ranges from about −50 mV to about −100 mV.

Clause 21. The method according to clause 19, wherein the maximum conductance of GABAergic synapses ranges from about 50% to about 100%.

Clause 22. The method according to clause 19, wherein the maximum conductance of AMPA synapses onto inhibitory neurons ranges from about 50% to about 100%.

Clause 23. The method according to clause 19, wherein the number of C fibers activated in each surround zone ranges from about 0% to about 50%.

Clause 24. The method according to clause 18, wherein the computational model simulates a response to an SCS pattern by varying the at least one stimulation input parameter, and wherein the at least one stimulation input parameter comprises: i) number of fibers activated within each network zone by an SCS pattern; and ii) stimulation frequency of an SCS pattern within each network zone.

Clause 25. The method according to clause 24, wherein the number of fibers activated within each network zone by the SCS pattern ranges from about 0% to about 100% in a first network zone, from about 0% to about 100% in a second network zone, and from about 0% to about 100% in a third network zone.

Clause 26. The method according to clause 24, wherein the stimulation frequency within each network zone ranges from about 1 Hz to about 200 Hz.

Clause 27. The method according to clause 18, wherein the computational model simulates a response to an SCS pattern by varying the at least one mechanism input parameter, and wherein the at least one mechanism input parameter comprises: i) maximum sodium conductance; and ii) maximum potassium conductance.

Clause 28. The method according to clause 27, wherein the maximum sodium conductance ranges from about 50% to about 150% within a network zone.

Clause 29. The method according to clause 27, wherein the maximum potassium conductance ranges from about 50% to about 150% within a network zone.

Clause 30. A system for delivering spinal cord stimulation (SCS) to reduce pain, the system comprising: an electrode sized and configured for implantation in proximity to neural tissue; and a pulse generator coupled to the electrode, the pulse generator including a power source comprising a battery and a microprocessor coupled to the battery, wherein the pulse generator is configured to generate electrical signals for delivering an SCS pattern having an optimized temporal pattern of electrical stimulation capable of reducing pain.

Clause 31. The system according to clause 30, wherein the optimized SCS pattern reduces pain in a plurality of subjects with different pain states.

Clause 32. The system according to clause 31 or clause 32, wherein the optimized SCS pattern comprises non-regular temporal patterns with one or more varying inter-pulse intervals.

Clause 33. The system according to any of clauses 30 to 32, wherein delivering an SCS pattern having an optimized temporal pattern of electrical stimulation comprises delivering one or more SCS patterns to one or more electrodes.

Clause 34. A method for delivering spinal cord stimulation (SCS) to reduce pain using the system of clause 26, the method comprising: programming the pulse generator to output the optimized SCS pattern; and delivering the SCS pattern to a subject to reduce pain.

Clause 35. The method according to clause 34, wherein the optimized SCS pattern reduces pain in a plurality of subjects with different pain states.

Clause 36. The method according to clause 34 or clause 35, wherein the optimized SCS pattern comprises non-regular temporal patterns with one or more varying inter-pulse intervals.

Clause 37. The method according to any of clauses 34 to 36, wherein delivering an optimized SCS pattern to a subject comprises delivering one or more different SCS patterns to one or more different neuronal populations.

What is claimed is:

1. A method of identifying an optimized spinal cord simulation (SCS) pattern for use in delivering electrical stimulation to a subject for pain reduction, the method comprising:
    generating a plurality of SCS patterns using an optimization algorithm based on predetermined performance criteria, wherein the predetermined performance criteria comprise variance of pain score reduction across different pain states;
    evaluating the plurality of SCS patterns for pain reduction using a computational model of a neuronal network;
    identifying at least one candidate SCS pattern having an optimized temporal pattern of stimulation capable of reducing pain; and
    delivering the at least one candidate SCS pattern to the subject using a neuromodulation device.

2. The method of claim 1, wherein the plurality of SCS patterns are generated for at least one of efficiency optimization, efficacy optimization, and variance optimization.

3. The method of claim 1, wherein the optimized SCS pattern reduces pain in a plurality of subjects with different pain states.

4. The method of claim 1, wherein the optimized SCS pattern comprises a temporal pattern of electrical stimulation pulses.

5. The method of claim 4, wherein the temporal pattern of electrical stimulation pulses comprises a non-regular temporal pattern with one or more varying inter-pulse intervals.

6. The method of claim 4, wherein the optimized SCS pattern comprises a stimulation frequency ranging from about 1 Hz to about 200 Hz.

7. The method of claim 1, wherein the optimization algorithm comprises at least one of a genetic algorithm, a particle swarm algorithm, a simulated annealing algorithm, an ant colony algorithm, an estimation of distribution algorithm, a gradient descent algorithm, and any combinations and derivations thereof.

8. The method of claim 1, wherein the predetermined performance criteria are incorporated into a fitness function used to evaluate the fitness of the plurality of SCS patterns.

9. The method of claim 1, wherein the predetermined performance criteria further comprise at least one of: i) reduction in pain score and/or ii) SCS pattern efficiency.

10. The method of claim 9, wherein the reduction in the pain score comprises a change in firing rate and/or firing pattern of one or more neurons in the computational model.

11. The method of claim 9, wherein the SCS pattern efficiency is proportional to average frequency of stimulation.

12. The method of claim 1, wherein the variance of pain score reduction across different pain states corresponds to variance of a response to SCS across a population of computational models of a neuronal network.

13. The method of claim 12, wherein the response to SCS comprises a change in firing rate and/or firing pattern of one or more neurons in the computational model.

14. The method of claim 1, wherein the computational model of the neuronal network is coupled to the optimization algorithm by the predetermined performance criteria.

15. The method of claim 1, wherein the computational model of the neuronal network simulates activity of a wide dynamic range (WDR) neuron.

16. The method of claim 15, wherein the activity of the WDR neuron in the computational model is a proxy for pain.

17. The method of claim 1, wherein the computational model of the neural network comprises three network zones comprising heterogeneous inhibitory and excitatory neural connections.

18. The method of claim 1, wherein the computational model of the neural network simulates a network state by varying at least one of: a biophysical input parameter, a stimulation input parameter, and a mechanism input parameter.

19. The method of claim 18, wherein the computational model simulates a pain state of a subject by varying the at least one biophysical input parameter, and wherein the at least one biophysical input parameter comprises: i) reversal potential of inhibitory synapses within a network zone; ii) maximum conductance of GABAergic synapses within a network zone; iii) maximum conductance of AMPA synapses onto inhibitory neurons within a network zone; and iv) number of C fibers activated in a surround zone.

20. The method of claim 19, wherein the reversal potential of inhibitory synapses ranges from about −50 mV to about −100 mV.

21. The method of claim 19, wherein the maximum conductance of GABAergic synapses ranges from about 50% to about 100%.

22. The method of claim 19, wherein the maximum conductance of AMPA synapses onto inhibitory neurons ranges from about 50% to about 100%.

23. The method of claim 19, wherein the number of C fibers activated in each surround zone ranges from about 0% to about 50%.

24. The method of claim 18, wherein the computational model simulates a response to an SCS pattern by varying the at least one stimulation input parameter, and wherein the at least one stimulation input parameter comprises: i) number of fibers activated within a network zone by an SCS pattern; and ii) stimulation frequency of an SCS pattern within a network zone.

25. The method of claim 24, wherein the number of fibers activated within a network zone by the SCS pattern (i) ranges from about 0% to about 100% in a first network zone, from about 0% to about 100% in a second network zone, and from about 0% to about 100% in a third network zone.

26. The method of claim 24, wherein the stimulation frequency within a network zone (ii) ranges from about 1 Hz to about 200 Hz.

27. The method of claim 18, wherein the computational model simulates a response to an SCS pattern by varying the at least one mechanism input parameter, and wherein the at least one mechanism input parameter comprises: i) maximum sodium conductance; and ii) maximum potassium conductance.

28. The method of claim 27, wherein the maximum sodium conductance ranges from about 50% to about 150% within a network zone.

29. The method of claim 27, wherein the maximum potassium conductance ranges from about 50% to about 150% within a network zone.

* * * * *